US008581582B2

(12) United States Patent
Miyazaki

(10) Patent No.: US 8,581,582 B2
(45) Date of Patent: Nov. 12, 2013

(54) MRI NON-CONTRAST TIME-SLIP ANGIOGRAPHY USING VARIABLY POSITIONED CINE SUB-SEQUENCE

(75) Inventor: Mitsue Miyazaki, Mount Prospect, IL (US)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 263 days.

(21) Appl. No.: 12/946,549

(22) Filed: Nov. 15, 2010

(65) Prior Publication Data

US 2011/0080170 A1    Apr. 7, 2011

(51) Int. Cl.
*G01R 33/48* (2006.01)

(52) U.S. Cl.
USPC .......................................... 324/309; 324/307

(58) Field of Classification Search
USPC .............................. 324/309; 600/410; 382/181
See application file for complete search history.

(56) References Cited

U.S. PATENT DOCUMENTS

| 6,271,665 | B1 | 8/2001 | Berr et al. |
| 6,564,080 | B1 | 5/2003 | Kimura |
| 6,782,286 | B2 | 8/2004 | Miyazaki |
| 6,801,800 | B2 | 10/2004 | Miyazaki et al. |
| 7,412,277 | B1 | 8/2008 | Saranathan et al. |
| 7,545,142 | B2 | 6/2009 | Alsop |
| 7,579,834 | B2 * | 8/2009 | Yui ................................ 324/307 |
| 7,613,496 | B2 | 11/2009 | Miyazaki et al. |
| 7,623,901 | B2 | 11/2009 | Kanazawa |
| 7,647,086 | B2 | 1/2010 | Miyazaki et al. |
| 2004/0049106 | A1 * | 3/2004 | Kanazawa ..................... 600/410 |
| 2008/0061780 | A1 | 3/2008 | Yamada et al. |
| 2009/0005670 | A1 | 1/2009 | Ichinose et al. |
| 2009/0143666 | A1 * | 6/2009 | Edelman et al. .............. 600/410 |

(Continued)

FOREIGN PATENT DOCUMENTS

| JP | 2001-149340 A | 6/2001 |
| JP | 2001-252263 | 9/2001 |

(Continued)

OTHER PUBLICATIONS

U.S. Appl. No. 12/722,875, filed Mar. 12, 2010, Yamashita.

(Continued)

*Primary Examiner* — Melissa Koval
*Assistant Examiner* — Rishi Patel
(74) *Attorney, Agent, or Firm* — Nixon & Vanderhye PC

(57) ABSTRACT

A magnetic resonance imaging (MRI) system using an MRI gantry and controlling computer system includes at least one programmed computer configured to effect a cardiac-triggered time-SLIP (spatial labeling inversion pulse) MRI data acquisition sequence for imaging blood perfusion in imaged patient tissue and employing therewithin an MRI cine sub-sequence. The sub-sequence is positioned in the time domain to encompass at least part of a predetermined (e.g., diastolic) cardiac time interval of the patient. Processing acquired data from the time-SLIP data acquisition sequence generates a sequence of MRI cine frame images having respectively associated different effective BBTI (black blood time to inversion) time intervals. Identifying one of the MRI cine frame images as acceptable, thereby effectively also determines an appropriate BBTI time interval for the patient. The system then outputs a time-SLIP image based on the determined appropriate BBTI time interval to at least one of (a) a display, (b) a remote system or (c) a non-transitory storage medium.

26 Claims, 4 Drawing Sheets

(56) References Cited

U.S. PATENT DOCUMENTS

| | | | |
|---|---|---|---|
| 2009/0148020 A1* | 6/2009 | Sugiura | 382/131 |
| 2010/0085051 A1* | 4/2010 | Littmann et al. | 324/309 |
| 2011/0071382 A1 | 3/2011 | Miyazaki et al. | |
| 2011/0074416 A1* | 3/2011 | Yamashita et al. | 324/309 |
| 2011/0080170 A1 | 4/2011 | Miyazaki | |

FOREIGN PATENT DOCUMENTS

| | | |
|---|---|---|
| JP | 2004-24637 A | 1/2004 |
| JP | 2005-531352 | 10/2005 |
| JP | 2006-198411 | 8/2006 |
| JP | 2009-028525 | 12/2009 |
| JP | 2011-83592 A | 4/2011 |

OTHER PUBLICATIONS

U.S. Appl. No. 12/763,643, filed Apr. 20, 2010, Miyazaki.

Zun, et al., "Assessment of Myocardial Blood Flow (MBF) in Humans Using Arterial Spin Labeling (ASL): Feasibility and Noise Analysis," *Magnetic Resonance in Medicine*, vol. 62, pp. 975-983 (2009).

Nishimura, et al., "Considerations of Magnetic Resonance Angiography by Selective Inversion Recovery," *Magnetic Resonance in Medicine*, vol. 7, pp. 482-484 (1988).

International Search Report mailed Jan. 24, 2012 in PCT/JP2011/076328.

Mitsue Miyazaki and Vivian S. Lee, "Nonenhanced MR Angiography," Radiology, Jul. 2008, vol. 248, No. 1, pp. 20-43.

* cited by examiner

__US 8,581,582 B2__

MRI NON-CONTRAST TIME-SLIP ANGIOGRAPHY USING VARIABLY POSITIONED CINE SUB-SEQUENCE

RELATED APPLICATIONS

This application is related to copending, commonly assigned, application Ser. No. 12/763,643 filed Apr. 20, 2010, which claims priority from Japanese application No. 2009/216,890 filed Sep. 18, 2009.

FIELD

The subject matter below relates generally to magnetic resonance imaging (MRI) processes. Preferably, the MRI processes described below involve enhancements to MRA (magnetic resonance angiography) images of myocardium tissue using time-SLIP (spatial labeling inversion pulse) imaging sequences.

DETAILED DESCRIPTION

Figure 1:
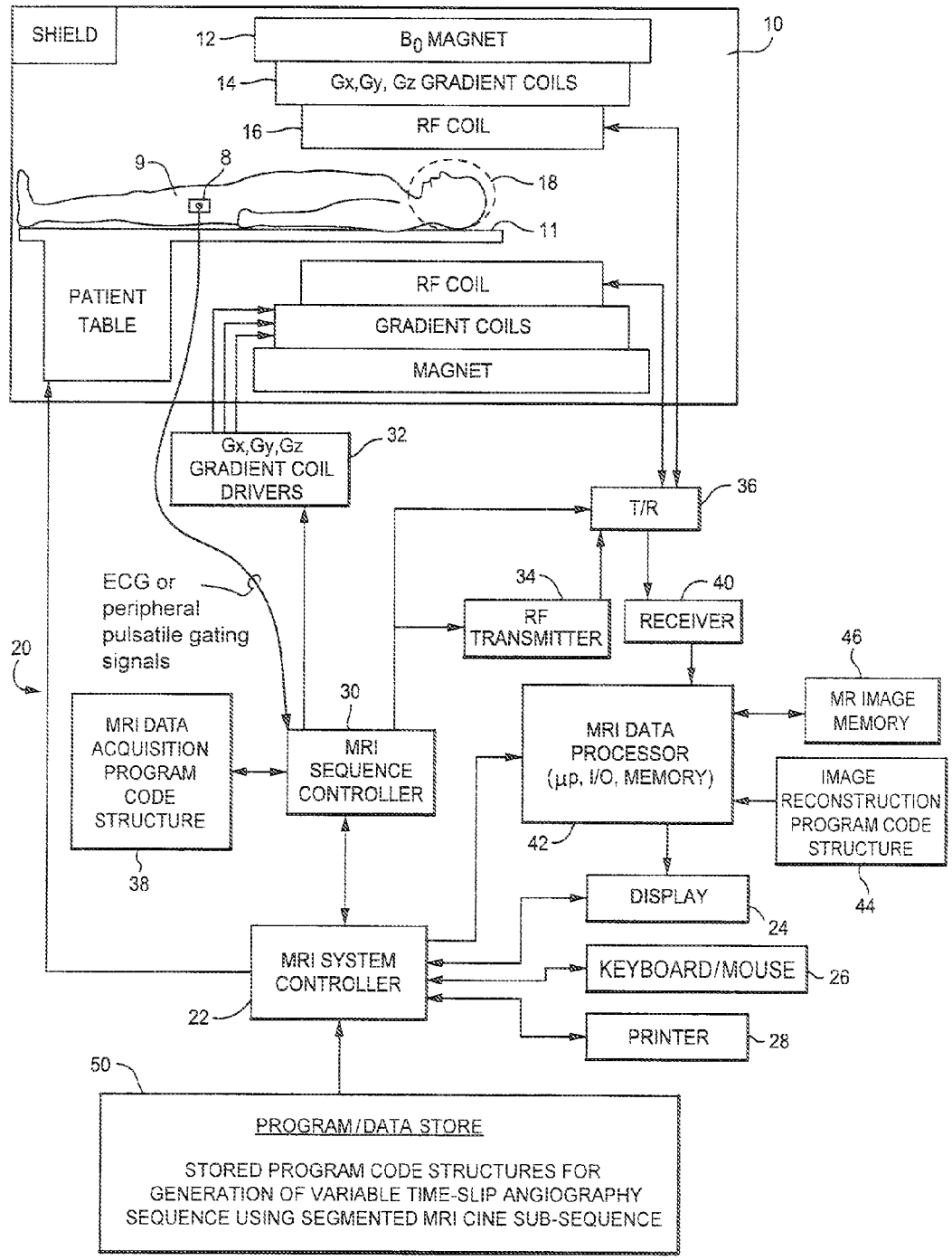
FIG. 1 is a high-level schematic block diagram of an exemplary MRI system embodiment adapted to acquire and process data for MRI using time-SLIP MRA where a MRI cine sequence helps determine an optimized BBTI (black blood time to inversion) interval.

The MRI system shown in FIG. 1 includes a gantry 10 (shown in schematic cross-section) and various related system components 20 interfaced therewith. At least the gantry 10 is typically located in a shielded room. One MRI system geometry depicted in FIG. 1 includes a substantially coaxial cylindrical arrangement of the static field B0 magnet 12, a $G_x$, $G_y$, and $G_z$ gradient coil set 14 and an RF coil assembly 16. Along the horizontal axis of this cylindrical array of elements is an imaging volume 18 shown as substantially encompassing the head of a patient 9 supported by a patient table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the $G_x$, $G_y$, and $G_z$ gradient coil drivers 32, as well as the RF transmitter 34 and the transmit/receive switch 36 (if the same RF coil is used for both transmission and reception). As those in the art will appreciate, one or more suitable body electrodes 8 may be affixed to the patient's body to provide ECG (electrocardiogram) and/or peripheral pulsatile gating signals to the MRI sequence controller 30. The MRI sequence controller 30 also has access to suitable program code structure 38 for implementing MRI data acquisition sequences already available in the repertoire of the MRI sequence controller 30 to generate time-SLIP and/or segmented cine MR images using operator and/or system inputs defining particular sequence parameters.

The MRI system 20 includes an RF receiver 40 providing input to data processor 42 so as to create processed image data to display 24. The MRI data processor 42 is also configured for access to image reconstruction program code structure 44 and to MR image memory 46 (e.g., for storing MR image data derived from processing in accordance with the exemplary embodiments and the image reconstruction program code structure 44).

Also illustrated in FIG. 1 is a generalized depiction of an MRI system program/data store 50 where stored program code structures (e.g., for generation of time-SLIP and cine MR images, operator inputs to same, etc.) are stored in computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those in the art will appreciate, the FIG. 1 depiction is a very high-level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast ND conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR-imaging reconstruction process, an array of computer-readable accessible data value storage sites (e.g., multi-digit binary representations of pixel values) in physical storage media will be transformed from some prior state (e.g., all uniform "zero" values or all "one" values) to a new state wherein the physical states at the physical sites of such an array (e.g., of pixel values) vary between minimum and maximum values to represent real world physical events and conditions (e.g., the tissues of a patient over an imaged volume space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to acquire and/or process MRI data acquisitions and/or to generate and display MR images.

MRI techniques for assessing myocardial blood flow using arterial spin labeling (ASL) are known. See, for example Zun, et al., "Assessment of Myocardial Blood Flow (MBF) in Humans Using Arterial Spin Labeling (ASL): Feasibility and Noise Analysis," *Magnetic Resonance in Medicine*, 62:975-

983 (2009), the entire content of which is hereby incorporated by reference. Here, a two-dimensional ASL sequence is used to study the tag on/off signal difference in the myocardium (with and without stress perfusion). See also the use of time-SLIP (spatial labeling inversion pulse) MRI techniques as described, for example, in related, copending, commonly assigned, application Ser. No. 12/763,643 filed Apr. 20, 2010, the entire content of which is hereby incorporated by reference. In this related application, a non-contrast cardiac perfusion time-SLIP technique has been used to observe "tagged" or "marked" flowing blood distribution by selecting an appropriate black-blood inversion time (commonly referred to as BBTI). However, the selection of an appropriate BBTI parameter value is critical, else the "tagged" blood flow bolus may not reach the imaged region of interest (ROI)—or may have already passed the ROI by the time MR image data is acquired. The problem of selecting an appropriate BBTI parameter value is especially difficult because it varies from patient to patient (and possibly varies even for a given patient depending upon heart rate and/or other patient-specific conditions).

Now, however, use of time-SLIP angiography incorporating a variably positionable cine sub-sequence can alleviate and/or eliminate the problem. In effect, in order to find a myocardial perfusion signal difference in good temporal resolution, a 2D cine sequence is used to study the signal intensity changes during desired cardiac phases (e.g., diastolic) of the myocardium. To study signal changes in cardiac phases using flow-out, 2D time-SLIP with balanced SSFP can be used.

In particular, an exemplary embodiment incorporating a cine sub-sequence (e.g., bSSFP or FFE in either two dimensions (e.g., one spatial dimension and one time dimension) or three dimensions (e.g., two spatial dimensions and one time dimension)) permits operator and/or system freedom to select a range of BBTI parameters for a given data acquisition sequence. For example, the duration of a segmented cine sub-sequence incorporated within the time-SLIP sequence can be controlled (e.g., by the operator or system)—as well as the subsequent recovery time (e.g., before a new data acquisition cycle) and any desired initial triggering delay (e.g., any delay subsequent to a selected triggering cardiac event before one or more RF tagging pulses are applied).

After data acquisition using this variably positionable cine sub-sequence in a time-SLIP data acquisition cycle, any required image subtraction or other processing/analysis of acquired signals can be automatically performed (e.g., with image position registration). Preferably, RF tag "on" and tag "off" parameters can be preselected by the operator (or system) so that the system can thereafter automatically perform plural data acquisition sequences, if appropriate, before performing necessary image differencing operations.

The end result can provide a displayed and/or stored (and/or exported to a remote system or site) indications of blood perfusion signal intensity changes within the imaged myocardium—either directly by using an identified one of the MRI cine frame images and/or by performing yet another (2D or 3D) time-SLIP data acquisition cycle—but now using the appropriate BBTI time interval parameter value as determined by previously identifying the most appropriate MRI cine frame image.

A time-SLIP sequence with an included cine sub-sequence may include, for example, (a) only a spatially-selective RF tag pulse applied upstream of the ROI so as to pursue a flow-in angiography approach, or (b) both a non-spatially-selective and a spatially-selective pulse applied to the ROI so as to effect a flow-out angiographic study. RF tag "on" and tag "off" data acquisition cycles may also be alternated to facilitate possible subtraction processing for angiographic outputs, as will be understood by those in the art. In some exemplary sequences, there are three effective time dimensions that can be controlled (e.g., an initial triggering delay, the duration of a segmented cine sub-sequence and a recovery time)—while in an alternate exemplary two-time dimensional scan, only the initial triggering delay and the duration of the cine sub-sequence may be selectable (e.g., by an operator and/or system programming). In any event, preferably the signal analysis processes are performed with due regard for image position registration where multiple images of the same ROI are involved (e.g., so as to compensate for possible motion artifacts between MRI cine frame images).

The use of time-SLIP data acquisition with an incorporated segmented cine sub-sequence results in depiction of signal changes during the patient's cardiac cycle (whether using a flow-in angiographic effect with only a single spatially-selective tag pulse) or a flow-out angiographic effect (using both non-selective and selective tagging pulses). In the flow-in approach, a spatially-selective tag pulse is applied to the myocardium and the myocardium MRI signal strength then decreases with increasing BBTI during a time-SLIP data acquisition sequence. In the flow-out approach, where non-selective and selective tag pulses are applied to an upstream portion of the myocardium, the MRI myocardium signal increases with increasing BBTI for a time-SLIP data acquisition sequence. In the alternate subtraction tag on/tag off approach, the myocardium signal increases with BBTI.

The tag on/tag off alternate acquisition scan approach helps to eliminate background signals while observing blood flow into the myocardium. In any event, MRI signal changes in intensity versus the on-going ever-increasing effective BBTI parameters during the cine sub-sequence effectively capture candidate BBTI parameter values for possible later use in a time-SLIP data acquisition sequence that does not use an incorporated cine sub-sequence (but instead uses some other desired MRI sequence). In addition, the selected MRI cine frame image (that can be used to determine the most appropriate BBTI time interval) may also possibly be usable itself as the output myocardial perfusion image.

For example, an initial time-SLIP sequence incorporating a cine sub-sequence may be achieved using only relatively quick and efficient two spatial dimensions of MRI so as to identify the appropriate BBTI parameter. Thereafter, a more lengthy three spatial dimensions time-SLIP data acquisition sequence may be performed (i.e., now without an incorporated cine sub-sequence) perhaps multiple times over plural slices so as to provide a three-dimensional image of the myocardium.

Figure 2:
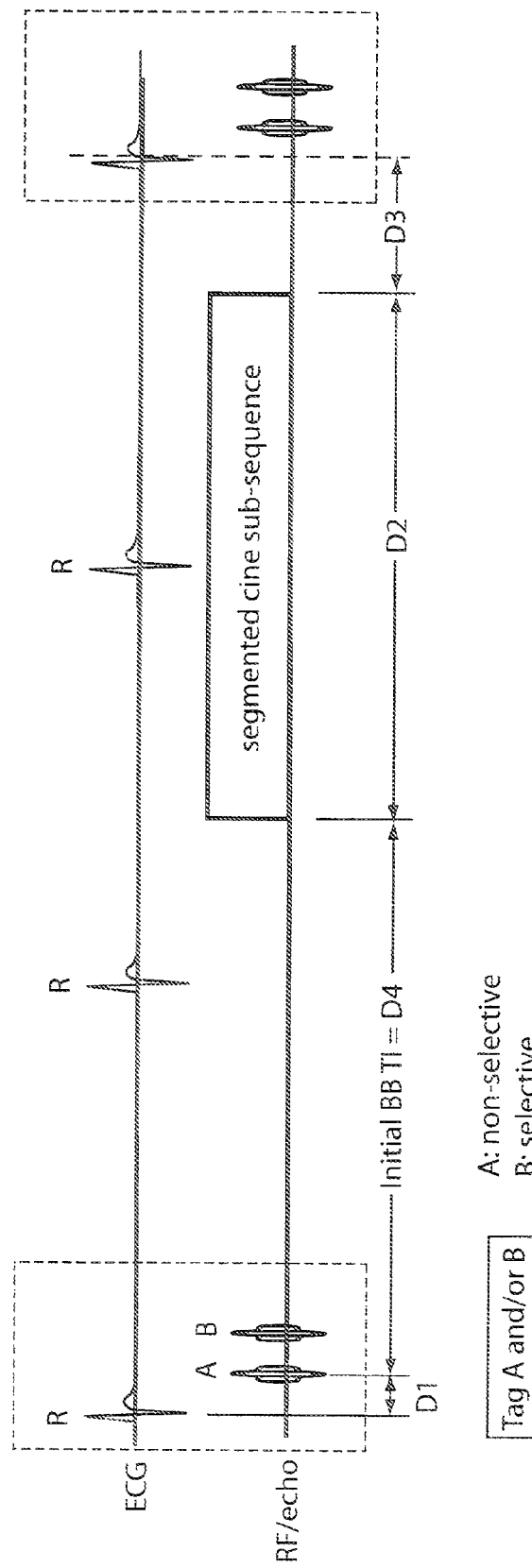
FIG. 2 is a schematic MRI sequence chart illustrating the use of a segmented cine sub-sequence to determine an optimum BBTI value and/or to provide an output MRA image.

An abbreviated exemplary time-SLIP data acquisition sequence using a variably positionable cine sub-sequence is schematically depicted in FIG. 2. The patient's electrocardiogram (ECG) signal R-waves are depicted on the top line in FIG. 2. RF tagging pulses (e.g., 180° nutation pulses) A and/or B may be applied starting after a typically short initial trigger delay D1 (which may approach zero in some embodiments). The usual magnetic gradient pulses are not shown explicitly in FIG. 2 to reduce complexity of the drawing. The duration of a segmented cine sub-sequence data acquisition (e.g., with a suitable initializing RF nutation pulse, SS, PE and RO magnetic gradient pulses, etc.) is depicted as having a time duration D2 (e.g., possibly 300-400 milliseconds hopefully covering at least the patient's cardiac diastolic period with perhaps 4-5 or so MRI cine frame images effectively taken at sequential BBTI delay times). The initial BBTI delay interval D4 (e.g., possibly 600 ms or so) is labeled in FIG. 2 as the delay from the initial triggering/tagging delay and the beginning of the segmented cine sub-sequence. After the segmented cine sub-sequence, a further recovery time delay D3 occurs before a subsequent data acquisition cycle begins (e.g., to permit the nuclear magnetization to return to a suitable starting condition). In an exemplary embodiment, the duration of one or more of these time intervals may be operator/system selectable so as to conform to a given patient's ECG signals (e.g., any three of D1, D2, D3 and/or D4 may effectively define the time intervals in the entire single sequence—or even fewer of such intervals can be defined by the operator, leaving the rest to system-defined defaults so long as an effort is made to place the cine sub-sequence such that it likely encompasses a desired part of a diastolic interval). In an exemplary embodiment, the use of a tag A pulse and/or a tag B pulse (or no tag pulse) may also be operator/system selectable/presettable. Application of a non-spatially-selective tag pulse A and a spatially-selective tag pulse B allows selectively marked or tagged blood to flow into the myocardium.

Figure 3:
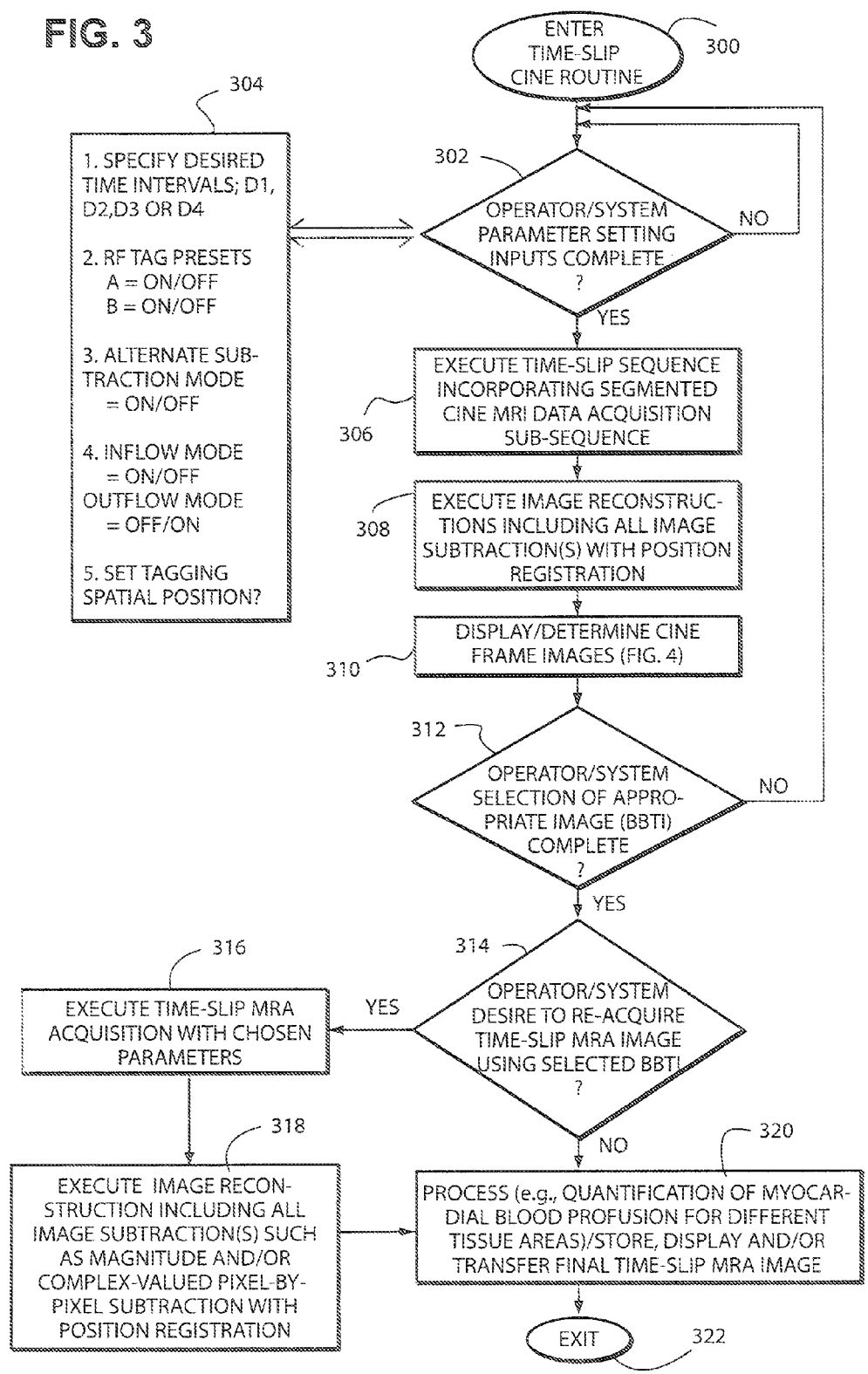
FIG. 3 is a schematic flow chart of exemplary computer program code structure that may be utilized for practicing an exemplary embodiment.

A high-level block diagram of exemplary controlling computer program code is depicted in FIG. 3. As those in the art will appreciate, entry into this time-SLIP cine routine may be had at 300 via either an operator- or system-imposed branch in a higher level controlling (e.g., operating system) computer program code. A wait loop 302 permits operator inputs to be completed (as specified, for example, in a graphical user interface (GUI) 304). Here, in one exemplary embodiment, some of the time intervals D1, D2, D3, D4 may be operator-selected at this point. In some embodiments, operator-selections may be used for only one or a few of these intervals, while system-selection may determine the remaining intervals. If the length of the total interval is known and there are n intervening time intervals, then no more than n−1 of the intervening time intervals need be defined by the operator and/or system. The tagging presets may be independently defined for both tag pulse A and tag pulse B, if desired (i.e., either or both may be preset to be "on" or "off"). Alternating on/off cycles for use in a subtraction mode may also be defined. The inflow mode or the out-flow mode may be alternatively selected—as may any related spatially-targeted tagging position (e.g., upstream of the ROI or within the ROI). As those in the art will appreciate, some or all of these data acquisition parameters may be system-selected and/or operator-selected via a suitable GUI.

In any event, once all of the data acquisition parameters have been suitably defined, then at 306, the defined time-SLIP sequence incorporating a cine sub-sequence is executed so as to acquire MRI data. Suitable cine sequences for use as the cine sub-sequence are known, per se. See, for example, related co-pending commonly assigned applications US 2008/0061780A1 (filed Sep. 10, 2007 and published Mar. 13, 2008; now U.S. Pat. No. 7,880,464 issued Feb. 1, 2011) and/or Ser. No. 12/722,875 filed Mar. 12, 2010 (now U.S. Pat. No. 8,427,149 issued Apr. 23, 2013), the entire contents of both of which are hereby incorporated by reference. Such cine sequences may also be referred to as segmented cine sequences (e.g., because such cine sequences may be segmented in at least k-space).

Figure 4:
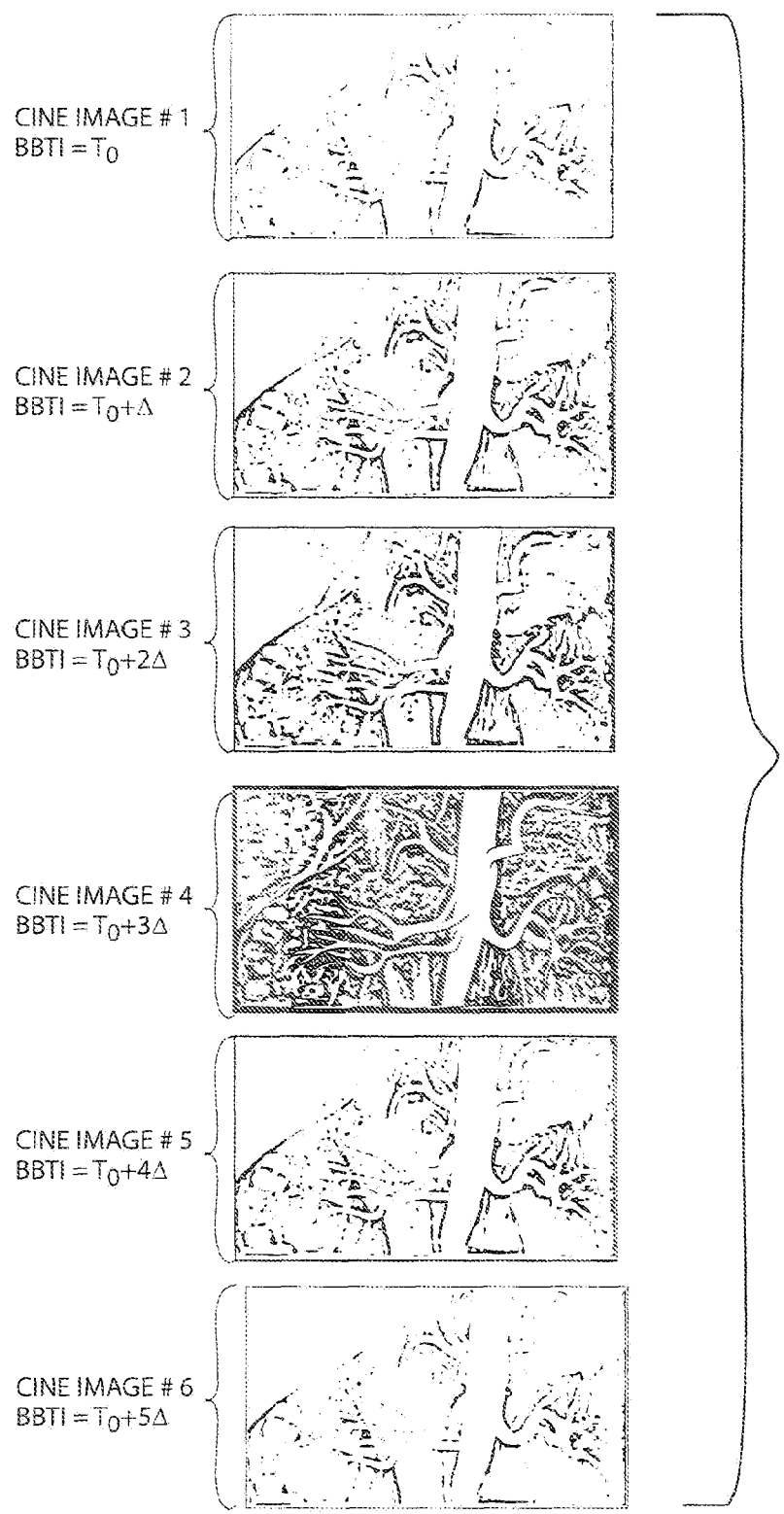
FIG. 4 is a schematic illustration of a possible screen display of MRI cine image frames demonstrating how an appropriate BBTI can be quickly determined for time-SLIP MRA.

At 308, suitable image reconstruction processes/signal processing steps are executed—automatically including all image subtraction processes, if required, using image position registration procedures therein. Thereafter, in this exemplary embodiment, the resulting cine frame images are displayed such as in FIG. 4. As will be seen in FIG. 4, of the successive cine image frames, frame 4 is the most clear and, therefore, the associated BBTI interval corresponding to that frame can be determined/identified as an appropriate BBTI time interval. As those in the art will appreciate, this identification of the appropriate MRI cine frame image and its corresponding BBTI interval may also be effected by suitable programmed computer processes without displaying them to the operator (as is also indicated at block 310 in FIG. 3). At decision block 312, a check is made to see whether the operator/system has concluded that an acceptable/appropriate BBTI interval has been identified/determined. If not, then control is returned to wait loop 302 for a new operator/system parameter setting input process, etc. However, if an appropriate image/BBTI interval has been selected/determined at 312, then a test is made at 314 to see whether there is an operator/system desire to reacquire a new time-SLIP MRA image using the just-determined BBTI interval (e.g., possibly now using a three-spatial dimension series of multi-slice data acquisition cycles may be desired). If so, then at 316, the time-SLIP MRA data acquisition cycles are executed with chosen parameters including the now identified appropriate BBTI parameter. The resulting acquired data is then processed through suitable image reconstruction processes executed at 318 including all, if any, required image subtraction(s) and again using suitable image position registration procedures as known in the art.

If a decision was made at 314 not to reacquire a new time-SLIP MRA image, then the previously selected MRI cine frame image (effectively already employing the identified appropriate BBTI parameter) is used as the final output. In any event, whether it is the selected cine frame image or an entirely new time-SLIP MRA image now using the identified appropriate BBTI parameter (based on processes at boxes 316, 318) input to the output box 320 in FIG. 3, the appropriate time-SLIP MRA output image may be further processed (e.g., by pixel-by-pixel subtraction image processes such as subtraction of the magnitude of pixel values in one image from the magnitude of corresponding pixel values in another image and/or subtraction of complex-valued pixels in one image from corresponding complex-valued pixels in another image so as to suitably quantify the perfusion of myocardial blood for different tissue areas, etc., in accordance with procedures already known by those skilled in the art), or be stored and/or displayed and/or transferred/exported to some other or remote facility/process/system before exit of this sub-routine is taken at 322.

While certain embodiments of the inventions have been described, these embodiments have been presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) system comprising an MRI gantry and controlling computer system including at least one programmed computer configured to:

effect a cardiac-triggered time-SLIP (spatial labeling inversion pulse) MRI data acquisition sequence for imaging blood perfusion in imaged patient tissue and employing embedded therewithin an MRI sequence, which MRI sequence is selectively positioned in the time domain so as to encompass at least part of a predetermined cardiac time interval of that particular patient's cardiac cycle;

process acquired data from the time-SLIP data acquisition sequence to generate a sequence of MRI images having respectively associated different effective BBTI (black blood time to inversion) time intervals;

process a plurality of the acquired MR images to generate blood perfusion information of said imaged patient tissue; and output said blood perfusion information to at least one of (a) a display, (b) a remote system or (c) a non-transitory storage medium.

2. An MRI system as in claim 1, wherein the position of said MRI sequence in the time domain is determined, at least in part, by at least one operator input defining at least one time interval occurring after a cardiac triggering event within the time-SLIP MRI data acquisition sequence.

3. An MRI system as in claim 2, wherein said at least one operator input includes specification of a plurality of: (a) an initial triggering delay which occurs immediately after said cardiac triggering event, (b) duration of said MRI sequence, (c) a recovery time which occurs after said MRI sequence and prior to a subsequent time-SLIP data acquisition sequence, and (d) an initial BBTI-related time delay before the start of the MRI sequence.

4. An MRI system as in claim 1, wherein said time-SLIP data acquisition sequence is defined and executed based, at least in part, upon at least one operator input defining at least one of the following sequence parameters: (a) use of spatially selective and/or spatially non-selective SLIP RF tag pulses, (b) use of plural data acquisition sequences with alternating on/off tagging and subtraction image processing, and (c) inflow or outflow MRA mode.

5. An MRI system as in claim 4 wherein said subtraction image processing includes at least one of: (a) pixel-by-pixel subtraction of the magnitude of pixel values in one image from the magnitude of corresponding pixel values in another image, and (b) pixel-by-pixel subtraction of complex-valued pixels in one image from corresponding complex-valued pixels in another image.

6. An MRI system as in claim 1, wherein said generation of blood perfusion information is based, at least in part, on a display of plural MRI images and a selective operator input identifying an image considered to be acceptable.

7. An MRI system as in claim 1, wherein said at least one programmed computer is configured to also:

effect a further time-SLIP data acquisition sequence for imaging blood perfusion in said imaged patient tissue using the BBTI time interval associated with an identified one of said sequence of MRI images.

8. An MRI system as in claim 6, wherein said at least one programmed computer is configured to effect said further time-SLIP data acquisition sequence for three spatial dimensions.

9. An MRI system as in claim 1, wherein said at least one programmed computer is configured to effect image position registration when processing said acquired data to generate a sequence of MRI images.

10. An MRI system as in claim 1, wherein the imaged blood perfusion is in imaged patient myocardium tissue.

11. An MRI system as in claim 1, wherein said at least one programmed computer is configured to output a quantified measurement of MRI signal intensity versus image time occurrence.

12. A magnetic resonance imaging (MRI) method comprising use of an MRI gantry and controlling computer system including at least one programmed computer configured to:

effect a cardiac-triggered time-SLIP (spatial labeling inversion pulse) MRI data acquisition sequence for imaging blood perfusion in imaged patient tissue and employing embedded there-within an MRI sequence, which MRI sequence is selectively positioned in the time domain so as to encompass at least part of a predetermined cardiac time interval of that particular patient's cardiac cycle;

process acquired data from the time-SLIP data acquisition sequence to generate a sequence of MRI images having respectively associated different effective BBTI (black blood time to inversion) time intervals;

process a plurality of the acquired MR images to generate blood perfusion information of said imaged patient tissue; and output said blood perfusion information to at least one of (a) a display, (b) a remote system, or (c) a non-transitory storage medium.

13. An MRI method as in claim 12, wherein the position of said MRI sequence in the time domain is determined, at least in part, by at least one operator input defining at least one time interval occurring after a cardiac triggering event within the time-SLIP MRI data acquisition sequence.

14. An MRI method as in claim 13, wherein said at least one operator input includes specification of a plurality of: (a) an initial triggering delay which occurs immediately after said cardiac triggering event, (b) duration of said MRI sequence, (c) a recovery time which occurs after said MRI sequence and prior to a subsequent time-SLIP data acquisition sequence, and (d) an initial BBTI-related time delay before the start of the MRI sequence.

15. An MRI method as in claim 12, wherein said time-SLIP data acquisition sequence is defined and executed based, at least in part, upon at least one operator input defining at least one of the following sequence parameters: (a) use of spatially selective and/or spatially non-selective SLIP RE tag pulses, (b) use of plural data acquisition sequences with alternating subtraction on/off tagging and image processing, and (c) inflow or outflow MRA.

16. An MRI method as in claim 15 wherein said subtraction image processing includes at least one of: (a) pixel-by-pixel subtraction of the magnitude of pixel values in one image from the magnitude of corresponding pixel values in another image, and (b) pixel-by-pixel subtraction of complex-valued pixels in one image from corresponding complex-valued pixels in another image.

17. An MRI method as in claim 12, wherein said generation of blood perfusion information is based, at least in part, on a display of plural MRI images and a selective operator input identifying an image considered to be acceptable.

18. An MRI method as in claim 12, wherein said at least one programmed computer is configured to also:

effect a further time-SLIP data acquisition sequence for imaging blood perfusion in said imaged patient tissue using the BBTI time interval associated with an identified one of said sequence of MRI image.

19. An MRI method as in claim 18, wherein said at least one programmed computer is configured to effect said further time-SLIP data acquisition sequence for three spatial dimensions.

20. An MRI method as in claim 12, wherein said at least one programmed computer is configured to effect image position registration when processing said acquired data to generate a sequence of MRI images.

21. An MRI method as in claim 12, wherein the imaged blood perfusion is in imaged patient myocardium tissue.

22. An MRI method as in claim 12, wherein said at least one programmed computer is configured to output a quantified measurement of MRI signal intensity versus image time occurrence.

23. A non-transitory computer memory medium containing computer program control code which, when executed by at least one programmed computer in a magnetic resonance imaging (MRI) system:

effects a cardiac-triggered time-SLIP (spatial labeling inversion pulse) MRI data acquisition sequence for imaging blood perfusion in imaged patient tissue and employing embedded there-within an MRI sequence, which MRI sequence is selectively positioned in the time domain so as to encompass at least part of a predetermined cardiac time interval of that particular patient's cardiac cycle;

processes acquired data from the time-SLIP data acquisition sequence to generate a sequence of MRI images having respectively associated different effective BBTI (black blood time to inversion) time intervals;

processes a plurality of the acquired MR images to generate a blood perfusion image of said imaged patient tissue; and outputs said blood perfusion information to at least one of (a) a display, (b) a remote system, or (c) a non-transitory storage medium.

24. A non-transitory computer memory medium as in claim 23 wherein said processes include at least one of: (a) pixel-by-pixel subtraction of the magnitude of pixel values in one image from the magnitude of corresponding pixel values in another image, and (b) pixel-by-pixel subtraction of complex-valued pixels in one image from corresponding complex-valued pixels in another image.

25. An MRI system as in claim 1, wherein:

said MRI data acquisition sequence is an MRI cine sub-sequence which acquires MRI data for a segment of k-space.

26. An MRI system as in claim 25, wherein:

said at least one programmed computer is further configured to identify one of the sequence of MRI images as having the highest contrast, thereby effectively also determining an appropriate BBTI time interval for the patient.

* * * * *